United States Patent [19]

Conrad et al.

[11] 4,363,754
[45] Dec. 14, 1982

[54] 4(5)-ACETYL-9,9-DIMETHYLTRICYCLO-[4,4,0,1^{8,10}]-UNDEC-1-ENE, ITS PREPARATION AND USE IN PERFUMERY COMPOSITIONS AND AS AN ODORANT

[75] Inventors: Jens Conrad, Hilden; Klaus Bruns, Krefeld-Traar; Horst Upadek, Erkrath, all of Fed. Rep. of Germany

[73] Assignee: Henkel Kommanditgesellschaft auf Aktien, Dusseldorf-Holthausen, Fed. Rep. of Germany

[21] Appl. No.: 317,017

[22] Filed: Nov. 2, 1981

Related U.S. Application Data

[62] Division of Ser. No. 178,083, Aug. 14, 1980, Pat. No. 4,322,559.

[30] Foreign Application Priority Data

Sep. 3, 1979 [DE] Fed. Rep. of Germany ....... 2935547

[51] Int. Cl.$^3$ ............................................... A61K 7/00
[52] U.S. Cl. ............................................... 252/522 R
[58] Field of Search ................................... 252/522 R

[56] References Cited

U.S. PATENT DOCUMENTS 3,835,192  9/1974  Van Der Linde et al. ......... 568/373
3,963,682  6/1976  Nagakurs et al. .................. 568/373
4,067,906  1/1978  Tavares et al. ..................... 568/373

FOREIGN PATENT DOCUMENTS 1192527  5/1970  United Kingdom ............... 568/373

Primary Examiner—Thomas A. Waltz
Attorney, Agent, or Firm—Hammond & Littell, Weissenberger and Muserlian

[57] ABSTRACT

4(5)-acetyl-9,9-dimethyltricyclo-[4,4,0,1$^{8,10}$]-undec-1-ene having the formula

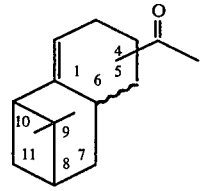

its synthesis, its use as a perfumery agent and as an olfactant component in perfumery compositions and as an odorant for technical products.

3 Claims, No Drawings

4(5)-ACETYL-9,9-DIMETHYLTRICYCLO-[4,4,0,1^{8,10}]-UNDEC-1-ENE, ITS PREPARATION AND USE IN PERFUMERY COMPOSITIONS AND AS AN ODORANT

This is a division of Ser. No. 178,083 filed Aug. 14, 1980, now U.S. Pat. No. 4,322,559.

BACKGROUND OF THE INVENTION

This invention relates to the isomeric mixture 4(5)-acetyl-9,9-dimethyltricyclo-[4,4,0,1$^{8,10}$]-undec-1-ene, its preparation and its use in perfumery. The compound is a valuable, new fragrance with a strong, warm, woody aroma.

OBJECTS OF THE INVENTION

An object of the present invention is the obtaining of the isomeric mixture 4(5)-acetyl-9,9-dimethyl-tricyclo-[4,4,0,1$^{8,10}$]-undec-1-ene.

Another object of the present invention is the development of a process for the production of said isomeric mixture 4(5)-acetyl-9,9-dimethyltricyclo-[4,4,0,1$^{8,10}$]-undec-1-ene.

A further object of the present invention is the development of a perfumery composition consisting essentially of from 1% to 50% by weight of the isomeric mixture 4(5)-acetyl-9,9-dimethyltricyclo-[4,4,0,1$^{8,10}$]-undec-1-ene and the remainder customary constituents of perfumery compositions.

A yet further object of the present invention is the development of a method of imparting a pleasant odor to a product comprising adding a sufficient amount of the above perfumery composition to provide the desired degree of odor.

These and other objects of the invention will become more apparent as the description thereof proceeds.

DESCRIPTION OF THE INVENTION

The above objects have been achieved by the novel isomeric mixture 4(5)-acetyl-9,9-dimethyltricyclo-[4,4,0,1$^{8,10}$]-undec-1-ene having the formula

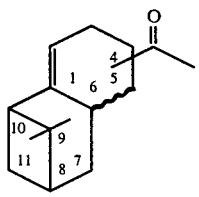

This isomeric mixture has physical properties and odorant properties that make it a valuable odorant with a strong, warm, woody scent and good odor persistency.

The new isomer mixture according to the invention is prepared by well-known methods of synthesis of organic chemistry. The commercial terpene derivative nopol is used as starting material for the systhesis. This can be dehydrated to nopadiene in a known manner, as described, for example, by Ohloff and Schade in Angewandte Chemie 67, 427 (1955). The isomer mixture according to the invention is obtained by the reaction of nopadiene with methyl vinyl ketone in a Diels-Alder reaction. For this purpose, it is most practical to heat the two starting components nopadiene and methyl vinyl ketone in the autoclave for several hours, at a temperature of about 160° C. The product obtained after fractionation is a mixture of structural or stereoisomers with respect to positions 4, 5 and 6. The synthesis is carried out according to the following reaction diagram:

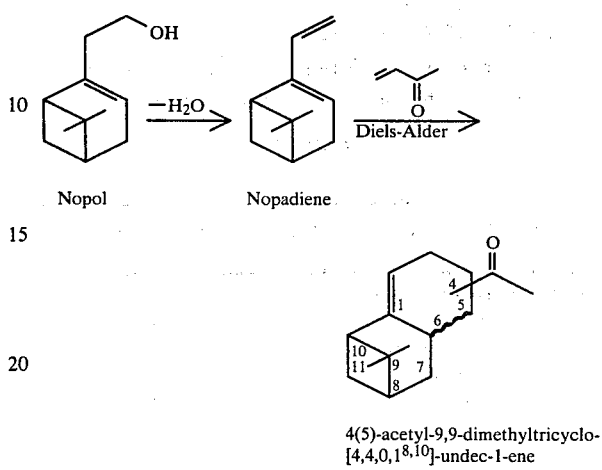

Nopol    Nopadiene

4(5)-acetyl-9,9-dimethyltricyclo-[4,4,0,1$^{8,10}$]-undec-1-ene

The new fragrance thus represents a mixture of the following structural isomers:
4-acetyl-9,9-dimethyltricyclo-[4,4,0,1$^{8,10}$]-undec-1-ene, and
5-acetyl-9,9-dimethyltricyclo-[4,4,0,1$^{8,10}$]-undec-1-ene.
In addition, the 5 and 6 carbon atoms can be in the cis or trans configuration, or a mixture.

The isomer mixture 4(5)-acetyl-9,9-dimethyltricyclo-[4,4,0,1$^{8,10}$]-undec-1-ene is characterized by a strong, warm, woody scent as well as a good staying power. Another advantage is its very good ability to combine into novel compositions, to which it lends a good staying power and interesting scent nuances as well.

The isomer mixture 4(5)-acetyl-9,9-dimethyltricyclo-[4,4,0,1$^{8,10}$]-undec-1-ene can be mixed with other fragrances in the most varied proportions to form new perfumery compositions. Its content in the perfumery compositions generally will be between 1% and 50% by weight, related to the total composition.

Such compositions can be used directly as perfumes or for perfuming cosmetic preparations such as cremes, lotions, colognes or toilet waters, aerosols, toilet soaps, etc. They also may be used to improve the smell of technical products such as washing and cleaning agents, softeners, and agents for the treating of textiles. For the scenting of the various products, the compositions generally are added to the former in concentrations of 0.05% to 2% by weight, related to the total product.

The following examples illustrate the subject matter of the invention in more detail without limiting it, however, to these examples.

EXAMPLE 1

Preparation of 4(5)-Acetyl-9,9-Dimethyltricyclo-[4,4,0,1$^{8,10}$]-undec-1-ene 148.2 gm (1 mol) of nopadiene freshly prepared from nopol and 70.1 gm (1 mol) of methyl vinyl ketone were heated for 6 hours in an autoclave under pressure of 5 bar of nitrogen at 160° C. After the removal of the foreruns by distillation, the crude product was fractionated under high vacuum. Obtained were 110 gm, that is, 50% of the theoretical yield, of the isomeric mixture of 4(5)-acetyl-9,9-dimethyltricyclo-[4,4,0,1$^{8,10}$]-undec-1-ene with the following analytical data:

Boiling point: 78–80° C. at 0.01 mbar.
Refractive index $n_D^{20} = 1.5132$.
IR (film): 1710 cm$^{-1}$ (ketone).
$^1$H-NMR(CCl$_4$): $\delta = 5.18$ ppm (m, 1H, C=CH).

The product had a strong, warm, woody scent.

EXAMPLE 2

| Fragrance Composition Woody Base for Men's Cologne | |
|---|---|
| | Parts by Weight |
| 4(5)-Acetyl-9,9-dimethyltricyclo-[4,4,0,1$^{8,10}$]-undec-1-ene | 300 |
| α-Hexylcinnamaldehyde | 80 |
| Linalyl acetate | 80 |
| Lyral (IFF) | 60 |
| γ-Methionone | 60 |
| Patchouli oil | 50 |
| Terpinyl acetate | 50 |
| Galaxolide (IFF) | 50 |
| Coumarin | 40 |
| Amyl salicylate | 40 |
| p-tert.-Butylcyclohexyl acetate | 40 |
| Benzyl acetate | 30 |
| Muscatel sage oil | 30 |
| Aldehyde C12 (10% in DPG) | 30 |
| Lemon grass oil | 20 |
| Vetiveryl acetate | 20 |
| Geranium oil | 10 |
| Rose oxide (10% in DPG) | 10 |
| | 1,000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A perfumery composition consisting essentially of from 1% to 50% by weight of the isomeric mixture 4(5)-acetyl-9,9-dimethyltricyclo-[4,4,0,1$^{8,10}$]-undec-1-ene and the remainder customary constituents of perfumery compositions.

2. The method of imparting a pleasant odor to a product comprising the step of adding a sufficient amount of the perfumery composition according to claim 1 to provide the desired degree of odor.

3. The method of claim 2 wherein the effective amount consists of from 0.05% to 5% by weight of the composition of claim 1.

* * * * *